United States Patent [19]

Davis

[11] 4,317,944

[45] Mar. 2, 1982

[54] PREPARATION OF 2,2-BIS(4-HYDROXYPHENYL) PROPANE

[75] Inventor: Gary C. Davis, Schenectady, N.Y.

[73] Assignee: General Electric Company, Schenectady, N.Y.

[21] Appl. No.: 178,515

[22] Filed: Aug. 15, 1980

[51] Int. Cl.$^3$ .............................................. C07C 39/16
[52] U.S. Cl. .................................. 568/728; 568/727
[58] Field of Search ................................ 568/728, 727

[56] References Cited

U.S. PATENT DOCUMENTS

| | | | |
|---|---|---|---|
| 3,264,357 | 8/1966 | Webb et al. | 568/728 |
| 3,367,979 | 2/1968 | Harper et al. | 568/727 |
| 4,052,466 | 10/1977 | Sun | 568/728 |
| 4,169,211 | 9/1979 | Ligorati et al. | 568/728 |

*Primary Examiner*—Werren B. Lone
*Attorney, Agent, or Firm*—Joseph T. Cohen; James C. Davis, Jr.

[57] ABSTRACT

The rate of reaction between acetone and phenol in the presence of an acidic catalyst to form 2,2-bis(4-hydroxyphenyl) propane can be accelerated by employing an aliphatic alcohol with the reactants.

11 Claims, No Drawings

PREPARATION OF 2,2-BIS(4-HYDROXYPHENYL) PROPANE

This invention is concerned with an improved process for making 2,2-bis(4-hydroxyphenyl) propane (hereinafter referred to as either "bisphenol-A" or "BPA"). More particularly, the invention is concerned with a process for accelerating the interaction of acetone and phenol in the presence of an acidic catalyst to make the aforesaid bisphenol-A by employing in the reaction mixture effective amounts of a saturated aliphatic alcohol.

Bisphenol-A has in the past been prepared by reaction between acetone and phenol in the presence of an acidic catalyst, such as HCl, sulfuric acid, cation exchange resins, etc. Although the method for making bisphenol-A has been fairly satisfactory, there are two objectives which would be desirable if they could be accomplished. In the first place, if the reaction between the acetone and phenol could be accelerated, this would mean that less time would be required for making the bisphenol-A thus freeing up equipment normally used for making the latter. In addition, in the separation of bisphenol-A, the o,p-isomer (hereinafter so designated) having the formula

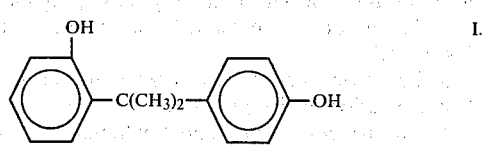

is obtained as part of the reaction product. In the manufacture of resins from the bisphenol-A, for instance, in the preparation of polycarbonate resins from the reaction of bisphenol-A and a carbonate precursor, such as diphenyl carbonate, phosgene, etc., it is important that most, if not all, of the o,p-isomer be removed before making such polycarbonate resins, in order to insure that the properties of the polycarbonate resins are at their maximum values. In order to remove the o,p-isomer, extra steps are usually required, such as crystallization, in order to insure that a minimum of the o,p-isomer remains in contact with the bisphenol-A.

I have now discovered unexpectedly that the incorporation of small amounts of a saturated aliphatic alcohol in the reaction mixture comprising the acetone, phenol, and the acidic condensation catalyst, markedly accelerates the rate of formation of bisphenol-A and usually reduces the amount of o,p-isomer which is formed. By means of my invention, the reaction for making the bisphenol-A can be accomplished at lower temperatures than is normally used and in shorter periods of time. The fact that the amount of o,p-isomer present, as a result of practicing my invention, is reduced, means that the amount of purification, for instance, by recrystallization can be considerably reduced, or timely and costly isomerization steps are greatly reduced or eliminated.

The aliphatic alcohols (hereinafter so designated), which include monohydric and polyhydric alcohols, are intended to include methanol, ethanol, propanol, ethylene glycol, 1,3-propanediol, 1,4-butanediol, 1,2-propanediol, 1,2-butanediol, pentaerythritol, glycerol, trimethylolpropane, etc. Generally, the aliphatic alcohol should be an aliphatic monohydric or polyhydric alcohol containing from 1 to 4 hydroxyl groups and having from 1 to 8 carbon atoms.

The amount of the aliphatic alcohol employed can be varied widely. Based on the acetone employed, one can use from 0.25 to 10 or more molar equivalents, preferably from 0.5 to 5 molar equivalents of the alcohol for each molar equivalent of acetone employed. Since the reaction is accelerated considerably as a result of the presence of the alcohol, the reaction can be conducted at somewhat lower temperatures than are normally used for making the bisphenol-A. The larger amounts of the aliphatic alcohol employed for the purpose in the reaction mixture are more than offset by the aforesaid advantageous features of the process and by reduced amounts of the o,p-isomer.

Although reaction can be conducted at normal pressures, generally it has been found that reaction between the acetone and phenol in the presence of the condensation catalyst can be advantageously carried out at superatmospheric pressures that range from about 5 to 50 psi or more in order to accelerate the rate of reaction still further.

The relative amount of phenol and acetone used can be varied widely. Generally, the phenol is employed in an excess and may range from about 2 to 10 or more mols of phenol per mol of acetone. The amount of acidic condensation catalyst employed can also be varied widely and may range from about 0.01 to 5% or more, by weight, based on the total weight of the phenol and acetone. Temperatures used for carrying out the reaction can range widely, for example, from about 30° to 100° C. or more, depending on the ratio of ingredients, the particular condensation catalyst, the kind and amount of the aliphatic alcohol used, etc. Generally, I have found that temperatures in the range of 40° to 75° C. are adequate for interacting the acetone and phenol to make the bisphenol-A within a reasonable time to give the desired product with a minimum amount of less desirable o,p-isomer.

In order that those skilled in the art might better understand how the present invention can be practiced, the following examples are given by way of illustration and not by way of limitation. All parts are by weight unless otherwise indicated.

EXAMPLE 1

To a pressure reactor equipped with a magnetic stirring bar and connected to a stainless steel inlet for introducing a gas was placed 5.03 grams (53.5 mmoles) phenol, 0.506 gram (8.71 mmoles) acetone and 1.083 grams (17.4 mmoles) ethylene glycol. The system was flushed with two 20 lb. charges of gaseous HCl and finally charged with 10 lbs. of gaseous HCl. The reaction mixture was then allowed to stir under pressure of about 10 psi at 50° C. for two hours. A precipitate comprising the adduct of bisphenol-A and phenol was formed within ¾ hour. The reaction mixture was analyzed by liquid chromatography. The results showed that 1.96 grams of product had formed (yield of about 98.7%) containing 4.99% of the o,p-isomer of formula I and the balance being bisphenol-A.

When a reaction similar to that described in Example 1 above was conducted, omitting ethylene glycol but otherwise being identical in reaction procedure and amounts of reactants and catalyst, only 1.02 grams of product was obtained representing a 52.9% yield of which 19.0% was the o,p-isomer of formula I and the balance was bisphenol-A.

EXAMPLE 2

In this example, other aliphatic alcohols were used with variations in the molar equivalents of alcohol (per equivalent of acetone) employed to form bisphenol-A. The following Table I shows the results of carrying out the reactions using the procedure described in Example 1. In one test, the pressure was increased to 15 psi; otherwise all of the tests conducted were at 10 psi. In addition, the following Table I also shows the effect of varying the time in which the reaction is carried out for the various alcohols as well as the effect of increasing the time of reaction (whether with or without the aliphatic alcohol). As the time of reaction is increased, it will be noted that the amount of o,p-isomer is reduced and this is believed due to the o,p-isomer undergoing an equilibration during the course of the reaction so that additionally formed bisphenol-A derived from the o,p-isomer is formed as a result of the equilibration. The presence of the saturated alcohol enhances the rate of this equilibration.

TABLE I

| Test No. | Aliphatic Alcohol | [1]Molar Equivalents Hydroxylated Compound | [2]Percent BPA | Time (hrs) | Pressure psi | Percent o,p-isomer |
|---|---|---|---|---|---|---|
| 1 | None | — | 52.9 | 2 | 10 | 16.4 |
| 2 | None | — | 95.1 | 6 | 15 | 4.4 |
| 3 | None | — | 97.5 | 20 | 10 | 1.3 |
| 4 | $CH_3OH$ | 1 | 81.5 | 2 | 10 | 5.8 |
| 5 | $CH_3OH$ | 1 | 96.3 | 6 | 10 | 2.2 |
| 6 | $CH_3OH$ | 2 | 80.5 | 2 | 10 | 4.6 |
| 7 | $CH_3OH$ | 4 | 76.9 | 2 | 10 | 5.1 |
| 8 | Ethylene Glycol | 1 | 92.6 | 2 | 10 | 7.8 |
| 9 | Ethylene Glycol | 2 | 98.7 | 2 | 10 | 5.0 |
| 10 | Ethylene Glycol | 2 | 96.5 | 7 | 10 | 1.8 |
| 11 | Ethylene Glycol | 4 | 92.1 | 2 | 10 | 5.3 |
| 12 | 1,3-Propanediol | 2 | 82.6 | 2 | 10 | 5.6 |
| 13 | 1,4-Butanediol | 2 | 68.3 | 2 | 10 | 6.5 |
| 14 | 1,2-Propanediol | 2 | 83.5 | 2 | 10 | 7.4 |
| 15 | 1,2-Butanediol | 2 | 76.2 | 2 | 10 | 8.5 |
| 16 | Pentaerythritol | 2 | 82.4 | 2 | 10 | 9.0 |
| 17 | Glycerol | 2 | 90.2 | 2 | 10 | 7.1 |
| 18 | Trimethylol Propane | 2 | 82.4 | 2 | 10 | 4.7 |

[1]Based on molar equivalents acetone
[2]Also indicates percent completion of reaction The fact that smaller amounts of the o,p-isomer are formed as a result of the practice of my invention indicates that one could also take the isolated o,p-isomer and in the presence of the acidic condensation catalyst, equilibration of the o,p-isomer would occur to form a mixture of the latter and additional bisphenol-A and that this equilibration could be accelerated by employing simultaneously one of the aliphatic alcohols herein described.

The bisphenol-A produced as a result of the practice of my invention has many uses. The greatest use involved making resins therefrom, such as epoxy resins, polycarbonate resins, etc. These resins can then be molded by injection, transfer, compression, or by any other technique to form molded articles, such as grill work for automobiles, housings for various equipment, castings for electrical coils, etc.

What I claim as new and desire to secure by Letters Patent of the United States is:

1. The process for accelerating the rate of formation of 2-bis(4-hydroxyphenyl) propane, which comprises heating a mixture of phenol and acetone in the presence of an acidic condensation catalyst and in the further presence of an effective amount of an aliphatic alcohol selected from the class consisting of methanol, ethanol, propanol, ethylene glycol, 1,3-propanediol, 1,4-butanediol, 1,2-propanediol, 1,2-butanediol, pentaerythritol, glycerol, and trimethylolpropane, and thereafter isolating the aforesaid hydroxyphenyl propane.

2. The process as in claim 1 wherein the acidic catalyst is HCl.

3. The process as in claim 1 wherein the acidic catalyst is a cation exchange resin.

4. The process as in claim 1 wherein the alcohol is ethylene glycol.

5. The process as in claim 1 wherein the alcohol is 1,3-propanediol.

6. The process as in claim 1 wherein the alcohol is 1,4-butanediol.

7. The process as in claim 1 wherein the alcohol is 1,2-propanediol.

8. The process as in claim 1 wherein the alcohol is pentaerythritol.

9. The process as in claim 1 wherein the alcohol is glycerol.

10. The process as in claim 1 wherein the alcohol is methanol.

11. The process as in claim 1 wherein at least 0.5 molar equivalent of the alcohol is employed per molar equivalent of acetone.

* * * * *